United States Patent [19]

De Ferra et al.

[11] Patent Number: 5,315,023

[45] Date of Patent: May 24, 1994

[54] PROCESS FOR THE PREPARATION OF GLYCEROPHOSPHOLIPIDS

[75] Inventors: Lorenzo De Ferra; Fausto Bonifacio; Guido Cifarelli; Pietro Massardo; Oreste Piccolo, all of Cinisello Balsamo, Italy

[73] Assignee: Chemi S.p.A., Patricia, Italy

[21] Appl. No.: 27,946

[22] Filed: Mar. 8, 1993

[30] Foreign Application Priority Data

Jun. 24, 1992 [IT] Italy ............................ MI92A001552

[51] Int. Cl.$^5$ ................................................ C07F 9/10
[52] U.S. Cl. .................................... 558/146; 558/145; 558/169
[58] Field of Search ................................. 558/145, 146

[56] References Cited

U.S. PATENT DOCUMENTS 5,100,787 3/1992 Shimizu et al. ..................... 435/131

Primary Examiner—Mary C. Lee
Assistant Examiner—Michael G. Ambrose
Attorney, Agent, or Firm—Oblon, Spivak, McClelland, Maier & Neustadt

[57] ABSTRACT

A process for the preparation of highly pure deacylated glycerophosphorylcholine, glycerophosphorylethanolamine and glicerophosphorylserine starting from mixtures of the corresponding acylated derivatives. The process according to the invention is characterized in that the deacylation reaction, by means of alcoholysis, and the fractionation are carried out in a single step in a reactor containing a basic ion-exchange resin.

14 Claims, No Drawings

PROCESS FOR THE PREPARATION OF GLYCEROPHOSPHOLIPIDS

The present invention relates to a new process for the preparation of deacylated phospholipids of formula (I)

wherein R is a residue of formula (II), (III) or (IV)

$$-CH_2CH_2NH_2, \quad (II)$$

$$-CH_2CH_2N^+(CH_3)_3, \quad (III)$$

$$-CH_2CH(NH_2)COOH, \quad (IV)$$

and X is OH when R is (II) or (IV) or X is O$^-$ when R is (III), starting from mixtures of the corresponding acylated derivatives of formula (V) of natural or synthetic origin,

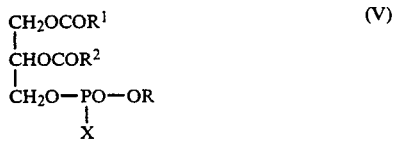

wherein X and R are as above defined and $R^1$ and $R^2$, which can be the same or different from each other, are $C_{13}$–$C_{25}$ alkyl, or $C_{13}$—$C_{25}$ mono or polyunsaturated alkenyl.

The process is characterized in that the deacylation reaction, by means of alcoholysis, and the fractionation are carried out in a single step in a reactor containing a basic ion-exchange resin.

The compounds I are obtained with high yield. The impurities of other than phospholipidic nature, which can optionally remain after the treatment with the basic ion-exchange resin, can be removed by means of several techniques, and preferably using the methods described hereinafter.

The importance of deacylated phospholipids (I) is well known and twofold. In fact, said compounds have recently gained a therapeutic importance, particularly for the treatment of involutive cerebral syndromes of different origin and of senile involution; on this purpose many references can be cited, as, for example, the International Patent Application WO 88/07860 relating to L-α-glycerophosphorylethanolamine (II) (hereinafter referred to as GPE); European Patent 0201623, relating to L-α-glycerophosphorylcholine (III) (hereinafter referred to as GPC); European Patent 0256069 relating to L-α-glycerophosphoryl-O-L-serine (hereinafter referred to as GPS). Further, the same derivatives (I) have been used as intermediates useful for the synthesis of other phosphatides, particularly of acylated derivatives of (V), containing specific $R^1$ and $R^2$ groups, which are widely used in the pharmaceutical field due to their intrinsic therapeutic activities and/or as liposomes capable of incorporating other active ingredients; other applications, as in cosmetics, electronics, etc., have further been described.

To date, the methods mostly used for the preparation of the compounds (I), having high chemical and optical purity degree, comprise:

a) the synthesis starting from expensive enantiomerically pure raw materials. For example (S)-2,2-dimethyl-1,3-dioxolan-4-methanol or (L)-glycerol-3-phosphate (see for instance a) J. Maurukas, C. V. Holland, J. Org. Chem. 26, 608 (1961); b) N. H. Phuong, N. T. Thuong, P. Chabrier, Bull. Chem. Soc. France 2326 (1975); c) M. Aloisi and P. Bffua, Biochem. J. 43, 157 (1948));

b) the deacylation reaction, usually in aqueous or alcoholic alkali conditions, of compounds (V), and subsequent purification of the obtained compounds (I).

Owing to the high cost and/or difficult availability, highly chemically pure compounds (V) can not be used as raw materials from an industrial point of view; accordingly deacylation reaction is carried out on more or less complex mixtures of compounds (V), which are obtained by extracting them from vegetable material or animal organs, are obtained by "transphosphatidylation" reaction, catalysed by phospholipase D (P. Comfurius, et al., Biochim. Biophys. Acta 488, 36 (1977) and L. R. Juneja et al., Biochim. Biophys. Acta 1003, 277 (1989)). Said mixtures may also contain other non-phospholipidic substances (Kirk-Othmer, ECT, 3° ed., vol. 14 page 261). The deacylation reaction, according to the reaction conditions (reaction time, temperature, base and solvent kind), may, in its turn, give rise to the formation of side products, such as for example D-1,2-glycerophosphate (E. H. Pryde, in "Lecithins" ed. B. F. Szuhay & G. R. List, AOCS Champaign IL, 1985, Cap. 11, pp 222–226), with yield losses and problems regarding the purification of the obtained products (I).

The use of methods b) to obtain compounds (I) on industrial scale implies severe problems, particularly as far as purification is concerned.

For example, GPC has been purified as described in literature (N.H. Tattrie, C. S. McArthur, Biochemical Preparations, 6, 16 (1958)), by forming complexes with metal salts, such as for example cadmium salts; and subsequently removing the metal by passing through an ion-exchange resin in the acid form; only after such a treatment it is possible to obtain crystalline GPC, which if it is not in highly pure form, does not crystallize. However, even the presence of trace amounts of very toxic metals hinders the industrial applicability of such a process.

In the EP 217765, after deacylation reaction of deoleated soy lecithin, the GPC-GPE mixture is purified from the other impurities by complexation with zinc salts, the decomplexation is subsequently performed by using pyridine derivatives and the GPC-GPE mixture is finally separated on strong basic ion-exchange resins eluting firstly with water to separate GPC, then with dilute aqueous acetic acid to recover GPE. A similar procedure, described in the Italian Patent Application 19895 A/90, allowed to separate mixtures containing GPS also; in this case, the GPS complex decomplexation was carried out treating in aqueous solvent with an acid ion-exchange resin. However said process is complicated because of the many steps required and the yields and optical purities are not satisfactory. Further, as remarked by the inventor themselves, in Italian Patent 1,229,238 the selection of alcoholic solvent to be used (ethanol vs. methanol) for deacylating reaction and zinc complexes formation constitutes a limitation which affect the yield and optical purity.

Chromatographic methods, which use expensive supports, as silica (E. Cubero Robles, G. F. M. Roels, Chem. Phys. Lipids, 6, 31 (1971)), are not suitable for a large scale separation., on the contrary, the use of chromatographies on ion exchange resins is convenient and industrially applicable. For example, according to European Patent Application 259495, partial or total fractionation of acylated glycerophospholipids can be obtained using acid and basic ion exchange resins, alone or admixed, in alcoholic solvents or alcohol-apolar solvent mixtures. Deacylated glycero-phospholipids fractionation on a strong basic ion exchange resins has been disclosed by J.N.Hawthorne, G. Huebscher, Biochem J. 71, 195 (1959) using a gradient eluent system.

The use of ion exchange resins in deacylated glycerophospholipids fractionation has further been developed in the Italian Patent 1,229,238, wherein GPC and GPE, obtained by soy lecithin deacylation with sodium methylate in methanol, are firstly adsorbed on acid ion exchange resins, then separated from other substances by eluting with an organic solvent, subsequently displaced from said resin by treating with water and subsequently fractionated on basic ion exchange resins, similarly to what above described.

As stated by the inventors, the operation on the acid resin must be carried out in controlled conditions and particularly within short times (in a similar process disclosed by the same inventors in Italian Patent Application 19895 A/90, Example 1, p. 19, the residence time on the column must not be longer than 1 hour to avoid the GPC and GPE decomposition, as it could be foreseen from literature data (E. Baer, M. Kates, J. Biol. Chem. 175, 79 (1948)); said limits become more evident when applied on the industrial scale.

The skilled technician can argue from the prior art the difficulty to prepare pure deacylated glycerophospholipids on industrial scale.

As to the deacylation reaction, a process drawn to the preparation of fat acids starting from phospholipids/alcohols mixtures has recently described in H. Tanaka et al., Jpn. Kokai Tokkyo JP 62215549. Said process uses a transesterification reaction catalyzed by basic ion exchange resins, similarly to what already described for neutral lipids (H. Schlenk, R. T. Holman, J.Am.Oil Chem. Soc. 30, 103 (1953)); however the Japanese reference fails to disclose the separation of compounds (I), which should form during said process.

It has now surprisingly been found that eluting an alcoholic mixture of compounds (V), moreover containing phosphatidylcholine, hereinafter named PC, phosphatidylethanolamine, hereinafter named PE, and/or phosphatidylserine, hereinafter named PS, in a reactor containing a basic ion exchange resins, according to the procedure described below, the corresponding fractionated compounds (I), namely GPC, GPE and/or GPS, can be obtained in a single step.

After elution from the basic ion exchange resins, GPC is easily purified from non phospholipidic impurities, such as fatty acid esters, and from other lipophilic impurities, by means of phase separation extraction or by treating with adsorption resins. GPC can be obtained in microcrystalline form by crystallization, for example from n-butyl alcohol.

GPE and/or GPS are then recovered from the resin by eluting with solvents containing organic acids, such as for example acetic acid, and after similar purification steps said compounds can be obtained in crystalline form.

In comparison with the known processes, the process of the present invention allows, to recover highly pure deacylated glycerophospholipids with a lower number of industrial operation, obtaining higher yields and avoiding the above mentioned problems of the prior art. A further advantage of the present process resides in obtaining the compounds (I), particularly GPC, in crystalline form.

Description of the process

A mixture of phospholipids (V), which are soluble in the alcoholic solvent used for the transesterification reaction (alcoholysis), was used as raw material on the basic ion exchange resins.

For example, the phospholipid mixture, which is obtained dissolving deoleated soy lecithin (a widely available low cost commercial product) in an alcohol and filtering the insoluble, can be used. As another example can be used phospholipids mixtures, obtained trough transphosphatidylation reactions catalysed by phospholipase D, for example a mixture of PS and PC recovered after treating the latter with serine.

The alcoholic solvent used as reagent in the alcoholysis reaction and as eluent on the resin is a $C_1$-$C_4$ alcohol, preferably methanol or ethanol, having water content $\leq 10\%$ v/v.

The basic ion exchange resin suitable for the process of the invention is commercially available or easily prepared and must be conditioned in the basic form in the presence of the alcohol used as reagent and eluent. The resin amount to be used, expressed in liters, shall range from 3 to 10 times, preferably from 4 to 5 times, the amount in kg of the compound (V) mixture. After loading the column with the alcoholic solution of the compounds (V), the elution is carried out with the same alcohol with a flow rate ranging from 0.1 to 0.4 bed volume/hour, preferably 0.2-0.3, until the complete GPC elution. The so obtained alcoholic solution, which contains GPC, fatty acid esters, and other non phospholipidic impurities, is neutralized with an inorganic or organic acid, preferably acetic acid, and subsequently concentrated to about 25% of the starting volume. Accordingly, two well separated phases are obtained, the upper one contains the fatty acid esters and other lipophilic impurities, the lower alcoholic one contains GPC.

Depending on which kind of GPC is to be obtained, two different procedures can be followed:

a) after further extraction with $C_6$-$C_{12}$ hydrocarbon mixtures or alternatively after removal of lipophilic impurities through apolar adsorption resins (such as for example Amberlite XAD 1600, marketed by Rohm & Haas), the lower alcoholic mixture is concentrated to small volume, recovered with a $C_2$-$C_6$ alcohol, preferably a $C_4$-alcohol, and GPC is obtained therefrom in a microcrystalline and anhydrous form;

b) alternatively, the same alcoholic phase is loaded on a ion exchange resins obtained by salifying a weak basic resin with an inorganic or organic acid, preferably hydrochloric or sulfuric acid, then said phase is eluted with an alcoholic solvent; due to this conditions the resin retains GPC only, which is subsequently eluted with water and the aqueous solution containing highly pure GPC is partially concentrated till the desired water content by evaporating under vacuum or by filloaded on a chromatographic column containing ion exchange resins Duolite A147 type in basic form conditioned in methanol. The elution was carried out with methanol until complete elution of the methaneluted compounds. Other compounds were then eluted with a 5% v/v acetic acid methanolic solution. GPS was finally eluted with a 5% acetic acid aqueous solution. The eluate containing GPS was vacuum concentrated. The residue was recovered with 8 ml of water, pH was adjusted to 4 with calcium carbonate, 3.2 ml of ethanol were added and 5.6 ml of acetone were then dropped in 4 minutes.

The crystallized product was filtered obtaining 0.65 g of (GPS)$_2$Ca as white crystalline solid.

We claim:

1. A process for the preparation of single deacylated phospholipids with high purity degree of formula (I)

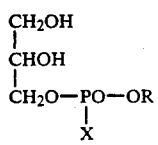
(I)

wherein R is a residue of formula (II), (III) or (IV)

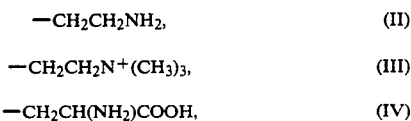

and X is OH when R is (II) or (IV) or X is O when R is (III), characterized in that acylated derivatives of formula (V) of natural or synthetic origin,

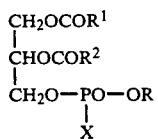
(V)

wherein X and R are as above defined and $R^1$ and $R^2$, which can be the same or different from each other are $C_{13}$-$C_{25}$ alkyl, or $C_{13}$-$C_{25}$ mono or polyunsaturated alkenyl, are subjected to deacylation reaction by means of alcoholysis and fractionation in a single step in a reactor containing a basic ion-exchange resin wherein said basic ion-exchange resin is conditioned in the basic form in the presence of the alcohol used for the alcoholysis.

2. A process according to claim 1, characterized in that the ion exchange resin amount to be used, expressed in liters, ranges from 3 to 10, times the amount in kilograms of the acylated derivatives of formula (V).

3. A process according to claim 2, wherein the ion-exchange resin amount, expressed in liters, is from 4 to 5 times the amount in kilograms of the acylated derivatives of formula (V).

4. A process according to claim 1 characterized in that the alcohol is a $C_1$-$C_4$ alcohol containing no more than 10% v/v of water.

5. A process according to claim 4, characterized in that the alcohol is methanol or ethanol containing no more than 10% v/v of water.

6. A process according to claim 1 characterized in that the resin elution is carried out with a flow rate ranging from 0.1 to 0.4 bed volume/hour with the same alcohol used for the alcoholysis till the complete glycerophosphorylcholine (GPC) outlet; then with the same alcohol containing 1-10% (v/v) of an organic acid, till the glycerophosphorylethanolamine (GPE) complete outlet; finally with water containing 1-10% (v/v) of an organic acid, till the glycerophosphorylserine (GPS) complete outlet.

7. A process according to claim 6, wherein the flow rate is from 0.2 to 0.3 bed volume/hour.

8. A process according to claim 7, characterized in that acetic acid is the organic acid.

9. A process according to claim 8, characterized in that the eluate containing GPC is concentrated to about ¼ of the starting volume, the so separated alcoholic phase, freed from optionally present lipophilic impurities by means of extraction with $C_6$-$C_{12}$ alkane mixtures or by passing through apolar adsorption resins, is concentrated to small volume and that GPC is crystallized from a $C_2$-$C_6$ alcohol.

10. A process according to claim 9, wherein n-butanol is the alcohol used for the crystallization.

11. A process according to claim 8 characterized in that anhydrous crystalline GPC is obtained.

12. A process according to claim 11, characterized in that the eluate containing GPC is a) loaded on a weak basic ion exchange resin, which has been salified with an organic or inorganic acid, b) freed from non phospholipidic impurities by eluting with the same alcoholic solvent, c) GPC is then eluted with water, d) the aqueous phase containing GPC is concentrated to the desired water content by vacuum evaporation and by filtration on nanofiltration membrane.

13. A process according to claim 12, characterized in that the eluate containing GPE, after having removed the optionally present lipophilic impurities by extracting them with $C_6$-$C_{12}$ alkane mixtures or by passing through apolar adsorption resins, is concentrated to small volume and GPC is finally crystallized.

14. A process according to claim 13, characterized in that the eluate containing GPS is concentrated to dryness and GPS is crystallized as calcium salt.

* * * * * tration through a suitable polymeric filtration membrane.

GPE and/or GPS recovery from the starting resin is performed after the complete GPC elution according to the following procedure.

GPE recovery

The resin is eluted with an alcoholic solution (preferably methanolic) containing an organic acid, preferably acetic acid, in a concentration comprised between 1% and 10% v/v; the eluted solution is concentrated, the solid impurities are filtered off and the lipophilic impurities are extracted whether with $C_6$-$C_{12}$ aliphatic hydrocarbons or through apolar adsorption resins; after concentrating to small volume, the residue containing highly pure GPE is crystallized from a 3:8 v/v water-ethanol aqueous mixture.

GPS recovery

After GPE removal, the resin is eluted with an aqueous solution containing an organic acid, preferably acetic acid, in a concentration comprised between 1% and 10% v/v; the eluted solution is concentrated to dryness, the residue GPS is crystallized as calcium salt from a 1:0.4:0.7 v/v water-ethanol-acetone mixture.

The following examples further illustrate the invention, without limiting it.

EXAMPLE 1

500 g of a commercially available mixture of phosphatidylcholine-enriched phospholipid mixture (phosphatidylcholine content: 53% w/w) were dissolved into 1.5 l of methanol, loaded on a chromatographic column containing 2 l of ion exchange resin Duolite A147 (Rohm & Haas) in basic form conditioned in methanol.

The column was eluted with methanol, subsequently the outlet solution was neutralized with acetic acid. The eluate (3.3 l) containing GPC, was concentrated to 0.75 l, the lower methanolic phase was separated and diluted with 100 ml of methanol and twice extracted with 800 ml of heptane. 2 l of n-butanol were added to the methanolic solution, the solvent was distilled under reduced pressure to 0.8 , l, cooled to 0° C. and filtered. After drying, 66.7 g of microcrystalline GPC were obtained.

In order to recover GPE, the column containing Duolite A147 resin was subsequently eluted with about 5 l of a 5% v/v acetic acid-methanol solution. The eluate was vacuum-concentrated to 0.5 l, the solids were filtered off and the filtrate was vacuum concentrated to 0.15 l. The solution was loaded on a chromatographic column containing 500 ml of water-conditioned Amberlite XAD 1600 (Rohm & Haas) adsorption resin. The column was eluted with 1.5 l of water, the eluate was vacuum concentrated and the obtained viscous oil was crystallized from a 8:3 ethanol-water mixture, obtaining 18.5 g of GPE.

By a similar procedure, except ethanol instead of methanol was used to dissolve the phospholipid mixture and to elute the Duolite A147 resin, a mixture having the above similar composition was obtained.

EXAMPLE 2

500 g of a commercially available mixture of phosphatidylcholine-enriched phospholipid mixture (phosphatidylcholine content: 53% w/w) were dissolved into 1.5 l of methanol, loaded on a chromatographic column containing 2 l of ion exchange resins Duolite A147 (Rohm & Haas) in basic form conditioned in methanol.

The column was eluted with methanol, subsequently the outlet solution was neutralized with acetic acid. The eluate (3.3 l) containing GPC, was concentrated to 0.75 l, the lower methanolic phase was separated and loaded on a chromatographic column containing 1 l of adsorption resin Amberlite XAD 1600. GPC was completely eluted with methanol, the residual lipophilic substances being not eluted by methanol.

GPC methanolic solution was vacuum-concentrated to 350 ml and loaded on a chromatographic column containing 2 l of ion exchange resin Amberlite IRA93SP (Rohm & Haas) in $Cl^-$ form conditioned in isopropanol. The impurities were completely eluted with isopropanol.

The elution was then carried out with demineralized water; the obtained GPC solution was neutralized with weak basic resin, treated with charcoal and vacuum concentrated to obtain GPC as a viscous liquid (84.5 g); water content =15%).

By a similar procedure, except using ion exchange resins Duolite A365 (Rohm & Haas) in $Cl^-$ form instead of Amberlite IRA93SP in $Cl^-$ form, GPC aqueous solution was obtained, which, after neutralizing with weak basic ion exchange resins and treating with charcoal, was concentrated with tangential filtration on a nanofiltration membrane. The concentration was completed by vacuum evaporation, obtaining 85.2 g of GPC as a viscous liquid with 16% water content.

EXAMPLE 3

1 l of methanol was added to 100 g of deoleated soy lecithin; the suspension was stirred for two hours at room temperature. The insoluble solids were filtered off and the solution was loaded on a column containing ion exchange resins Duolite A147 in basic form conditioned in methanol. The column was eluted with methanol until complete GPC elution, neutralizing the methanolic solution with acetic acid. The solution was concentrated until a clear phase separation was obtained, the phases were separated, the methanolic phase was twice extracted with 300 ml of hexane. The methanolic solution was loaded on a column containing ion exchange resins Amberlite IRA93SP in $Cl^-$ form conditioned in isopropanol. The impurities were completely eluted with isopropanol.

The elution was then carried out with demineralized water; the obtained GPC solution was neutralized with weak basic resin, treated with charcoal and concentrated with tangential filtration on a nanofiltration membrane.

The concentration was completed by vacuum evaporating the solvent. Highly pure GPC was obtained in the form of a viscous liquid.

EXAMPLE 4

100 g of soy lecithin (ethanol-soluble, phosphatidylcholine-enriched fraction) were dissolved into 300 ml of methanol and loaded on a column containing 400 ml of weak basic ion exchange resin Amberlite IRA 94 S in basic form, conditioned in methanol. The elution was carried out in methanol; the eluate containing GPC was collected and vacuum concentrated, the phases were separated and, following the procedure of Example 1, 13.5 g of crystallized GPC were obtained.

EXAMPLE 5

400 ml of ethanol containing 7 g of a phospholipid mixture, of which 41% were phosphatidylserine, were